United States Patent

Menta et al.

[11] Patent Number: 6,034,092
[45] Date of Patent: *Mar. 7, 2000

[54] 2-[2-[(2-HYDROXYETHYL)AMINO]ETHYL]-5-[[2-METHYLAMINO)ETHYL]AMINO] INDAZOLO[4,3-GH]ISOQUINOLIN-6(2H)-ONE AS ANTITUMOR AGENT

[75] Inventors: Ernesto Menta; Ambrogio Oliva; Silvano Spinelli; Paul Krapcho, all of Monza, Italy

[73] Assignee: Novuspharma S.p.A., Milan, Italy

[ * ] Notice: This patent is subject to a terminal disclaimer.

[21] Appl. No.: 09/029,742

[22] PCT Filed: Sep. 9, 1996

[86] PCT No.: PCT/EP96/03935

§ 371 Date: Jun. 22, 1998

§ 102(e) Date: Jun. 22, 1998

[87] PCT Pub. No.: WO97/10245

PCT Pub. Date: Mar. 20, 1997

[30] Foreign Application Priority Data

Sep. 13, 1995  [IT]  Italy ................................. MI95A1904

[51] Int. Cl.[7] ..................... C07D 471/06; C07D 221/18; A61K 31/435
[52] U.S. Cl. ............................ 514/287; 546/101
[58] Field of Search ............... 514/287; 546/101

[56] References Cited

U.S. PATENT DOCUMENTS 5,519,029  5/1996  Krapcho et al. .................. 514/287

*Primary Examiner*—Alan L. Rotman
*Attorney, Agent, or Firm*—Nikaido Marmelstein Murray & Oram, LLP

[57] ABSTRACT

The present invention relates to 2-[2-[(2-hydroxyethyl) amino]ethyl]-5-[[2-methylamino)ethyl]amino]indazolo[4,3-gh]isoquinolin-6(2H)-one and the pharmaceutically acceptable acid addition salts thereof, of formula (I). This compound has shown a high a antitumor activity.

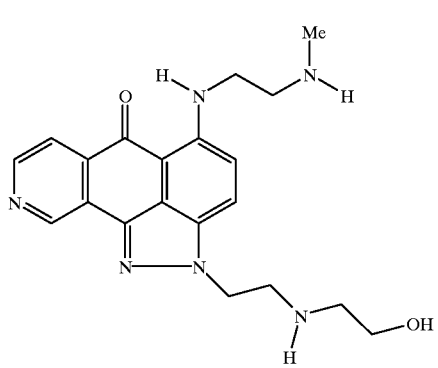

(I)

7 Claims, No Drawings

2-[2-[(2-HYDROXYETHYL)AMINO]ETHYL]-5-[[2-METHYLAMINO)ETHYL]AMINO] INDAZOLO[4,3-GH]ISOQUINOLIN-6(2H)-ONE AS ANTITUMOR AGENT

CROSS-REFERENCE

This application is a 371 of PCT/US96/03935 filed Sep. 9, 1996.

The present invention relates to 2-[2-[(2-hydroxyethyl)amino]ethyl]-5-[[2-methylamino)ethyl]amino]indazolo[4,3-gh]isoquinolin-6(2H)-one and the pharmaceutically acceptable acid addition salts thereof.

This compound has shown a high antitumor activity.

PRIOR ART

Some 1,4-bis[(aminoalkyl)amino]anthracene-9,10-diones have shown antitumor activity in clinical trials. Particularly interesting are ametantrone, 4-bis{[2-(2-hydroxyethylamino)ethyl]amino]anthracene-9,10-dione and mitoxantrone, 5,8-dihydroxy-1,4-bis{[2-(2-hydroxyethylamino)ethyly]amino]anthracene-9,10-dione. (Zee-Cheng et al., *J. Med. Chem.*, (1978), 21, 291–4; Cheng et al., "Progress in Medicinal Chemistry", Ellis, G. P. and West, G. B., eds.; Elsevier: Amsterdam, 1983; pp. 20, 83 and references cited therein). Mitoxantrone is a broad spectrum oncolytic agent, whose activity is similar to that of the anthracycline antibiotic doxorubicin. Clinical trials have demonstrated that mitoxantrone has particularly promising activity in the treatment of advanced breast cancer, acute leukemia and lymphoma (Legha, *Drugs of Today*, (1984), 20, 629). The limiting aspect of these medicaments is the cardiotoxicity, particularly with mitoxantrone, and the mielodepressive toxic effect of both of them. In addition, both compounds show cross-resistance towards the cell histotypes developing resistance already against doxorubicin, said resistance being mediated by over-expression of glycoprotein P. Such a resistance, which is named multidrug resistance, involves a number of antitumor antibiotics, among which amsacrine and podophyllotoxin and derivatives, and it is one of the main reasons for therapeutical failures in the treatment of solid tumors with said antibiotics.

In an attempt to overcome these drawbacks, some anthracenediones with the chromophor modified were prepared. For example, EP-A 103,381 claims 2-aminoalkyl-5-aminoalkylamino anthra[1,9-cd]pyrazol-6(2H)-ones (anthrapyrazoles) with antitumor activity. The antitumor activity of said compounds in pre-clinic trials has been reported by H. D. Hollis Showalter et al. (J. Med. Chem., 30, 121–131 (1987)).

However, anthrapyrazoles are not devoid of toxic side-effects, such as severe leukopenia (W.H.O. grade 3 and 4) and neutropenia (W.H.O. grade 4) which turned out to be dose-limiting in clinical trials of phase I and II with anthrapyrazole CI-941 [I. E. Smith et al., J. Clin. Oncol., 9, 2141–2147 (1991)]. Moreover, a marked nephrotoxicity is associated with the treatment with CI-941 in the rat [D. Campling e M. E. C. Robbins, Nephrotoxicity, Peter H. Dekker Bach and., Pag. 345–352 (1991), New York: vedi Chem. Abstracts 116: 294n (1992)] and these authors suggest that the renal damage could be a clinical problem of the anthrapyrazole therapy. Moreover, recent works [Drugs of the Future, 17, 725 (1992); Judson, I. R. et al., Proc. Amer. Assoc. Cancer Res., 32, abstr. 1059 (1991)] show that anthrapyrazole CI-941 induces irreversible cardiotoxicity in man, even though no symptoms of acute cardiac events have ever been reported.

From what stated above, the search for novel active analogues is still highly desirable.

Anthrapyrazole aza-analogues, in which the nitrogen has been introduced at the 8- and 9- positions, are described in PCT/US93/08241 (published on Mar. 31, 1994, WO94/06795). Said compounds have evidenced a high antitumor activity both on in vitro and in vivo models and, contrary to doxorubicin and mitoxantrone, showed no cross-resistance on the LoVo/DX cell line. These data allow to envisage a possible activity in clinic on leukemias and solid tumors sensitive to the treatment with antitumor antibiotics.

Now it has been found that an anthrapyrazole 9-aza-analogous, 2-[2-[(2-hydroxyethyl)amino]ethyl]-5-[[2-(methylamino)ethyl]amino]indazolo[4,3-gh]isoquinolin-6(2H)-one, has a surprising activity which makes it markedly different from the other derivatives of this series. Said compound, in fact, in addition to an higher increase in the average survival time of the treated animals (expressed as % T/C) than that obtained with its analogues, has moreover evidenced a complete regression of the tumor in a statistically significant number of animals and therefore it is believed to be effective in clinical trials.

DISCLOSURE OF THE INVENTION

The present invention relates to 2-[2-[(2-hydroxyethyl)amino]ethyl]-5-[[2-methylamino)ethyl]amino]-indazolo[4,3-gh]isoquinolin-6(2H)-one of formula (I) and the pharmaceutically acceptable acid addition salts thereof:

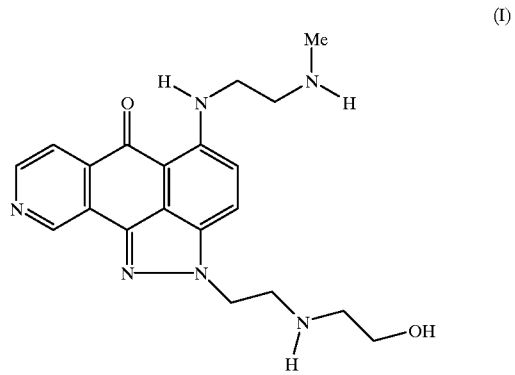

(I)

Examples of pharmaceutically acceptable acids are: inorganic acids such as hydrochloric, hydrobromic, sulfuric, nitric, phosphoric, pyrophosphoric acids or organic acids such as acetic, trifluoroacetic, propionic, citric, benzoic, lactic, maleic, malic, fumaric, succinic, tartaric, glutamic, aspartic, gluconic, ascorbic, p-toluenesulfonic, methanesulfonic acids or other conventionally used acids.

More particularly, the invention relates to 2-[2-[(2-hydroxyethyl)amino]ethyl]-5-[[2-methylamino)ethyl]-amino]indazolo[4,3-gh]isoquinolin-6(2H)-one trihydrochloride.

The compound of the invention can be prepared starting from the intermediate of formula (II):

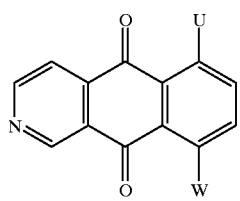

(II)

in which U is selected from the group consisting of F, Cl, para-toluenesulfonyloxy (OTs), methanesulfonyloxy (OMs), whereas W is F or Cl, with the proviso that U and W cannot be at the same time Cl, by reaction with an hydrazine of formula (III):

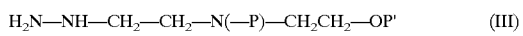

H$_2$N—NH—CH$_2$—CH$_2$—N(—P)—CH$_2$CH$_2$—OP'  (III)

in which P and P' can be independently hydrogen or a suitable protective group stable in the reaction conditions.

The resulting compounds of formula (IV):

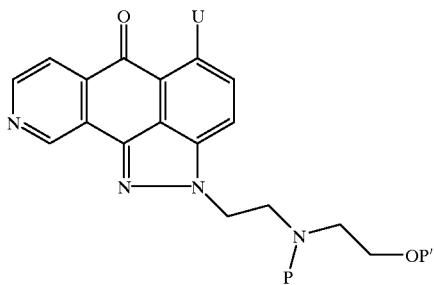

(IV)

are then converted into the compound of formula (I) by reaction with amines of formula (V):

H$_2$N—CH$_2$CH$_2$—N(—P)Me  (V)

in which P has the meanings defined above, and subsequent cleavage of any protective groups P and P' present. In this instance, a salt of the compound of formula (I) will be obtained, the counter-ion of which is a function of the acid used for the cleavage reaction. If gaseous hydrochloric acid in excess is used, the compound (I) will be obtained as the trihydrochloride.

A preferred method for the synthesis of the compound of formula (I) is that involving the reaction of the intermediate of formula (II'):

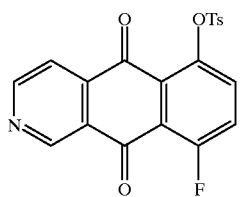

(II')

with an hydrazine of formula (III) and then with an amine of formula (V) and the subsequent cleavage of any protective groups P and P' present. Examples of protective groups P and P' are: (C$_1$–C$_3$)-acyl derivatives (preferably acetyl), (C$_1$–C$_4$)-alkoxycarbonyl derivatives (preferably tert-butoxycarbonyl) and (C$_7$–C$_{10}$)-aralkyloxy-carbonyl derivatives (preferably benzyloxycarbonyl).

The reaction of the intermediates of formula (II) with the hydrazines of formula (III) can be carried out heating the intermediates (II) with a stoichiometric amount or with an excess of hydrazines (III). The reaction is usually carried out in a inert solvent such as methylene chloride, chloroform, 1,1,1-tricloroethane, dimethoxyethane, tetrahydrofuran, dimethylsulfoxide, dimethylformamide, pyridine, picoline, alcohols (methanol, ethanol) or in mixtures thereof (alternatively, the compounds (III) can be used alone as the solvent), in presence of an optional inorganic base such as an alkali or alkaline-earth metal carbonate or hydrogen carbonate or an organic base such as trialkylamine, at a temperature ranging between −20° C. and the solvent boiling temperature. Preferably, the reaction is carried out in a solvent such as pyridine, tetrahydrofuran, dimethylsulfoxide or N,N,N', N'-tetramethylethylenediamine, using 2 to 10 equivalents of hydrazines (III) and operating at a temperature ranging between 5° C. and 50° C.

The reaction of the intermediate of formula (II') with the hydrazines of formula (III) can be carried out preferably in a solvent capable of dissolving the reagents, such as a mixture of tetrahydrofuran and of an alcohol (ethanol, methanol), and a temperature ranging between −10° C. and room temperature.

The reaction of a compound of formula (IV) with an amine of formula (V) can be carried out heating the compound (IV) with a stoichiometric amount or with an excess of amine (V). The reaction is usually carried out in an inert solvent such as methylene chloride, chloroform, 1,1,1-tricloroethane, dimethoxyethane, tetrahydrofuran, dimethylsulfoxide, dimethylformamide, pyridine, picoline or mixtures thereof or, if desired, using the amine (V) itself as the solvent, optionally in the presence of an inorganic base such as an alkali or alkaline-earth carbonate or hydrogen carbonate or of an inorganic base such as a trialkylamine, at a temperature ranging between 0° C. and the solvent boiling temperature.

Preferably the reaction is carried out in a solvent such as pyridine, chloroform or dimethylsulfoxide, using 2 to 10 equivalents of amine (V) and operating at a temperature ranging between room temperature and 100° C.

The reaction of an intermediate of formula (IV) in which U is OTs with an amine of formula (V) can be carried out in solvents such as pyridine or dimethylsulfoxide and a temperature ranging between room temperature and 100° C.

The cleavage of any protective groups P and P' can be carried out according to procedures well-known to those skilled in the art, such as for example those described in Green, T. W., Wuts, P. G. M., "Protective Groups in Organic Synthesis", second edition, John Wiley & Sons, 1991.

For example, the cleavage of a N-tert-butoxycarbonyl group can be obtained by treatment of the protected intermediate with an excess of anhydrous hydrogen chloride, in a solvent such as ethanol, methanol, dichloromethane, chloroform or mixtures thereof, at a temperature ranging between 20° C. and 50° C. and for a reaction time comprised between a few minutes and some hours.

The compound of formula (II') can be prepared starting from the compound (VI):

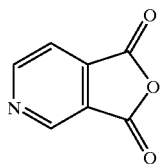

(VI)

by means of a Friedel-Crafts acylation of 1,4-difluorobenzene, in the presence of $AlCl_3$ at about 90° C. for about 22 hours, which leads to a mixture of the (VIIa) and (VIIb) regioisomers:

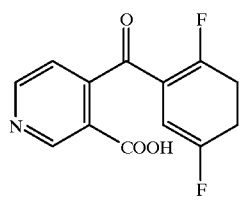

(VIIa)

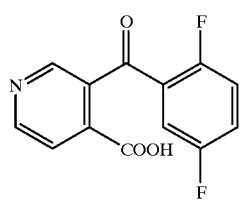

(VIIb)

Alternatively, the mixture of regioisomers (VIIa) and (VIIb) can be obtained reacting the intermediate (VI) with 1-lithium-2,5-difluorobenzene, prepared by reaction of 1,4-difluorobenzene with an alkyl-lithium such as sec-butyl lithium in THF at low temperature.

The mixture of regioisomers (VIIa) and (VIIb) is then cyclized with oleum (20% $SO_3$) at 130–140° C. to obtain the compound (VIII):

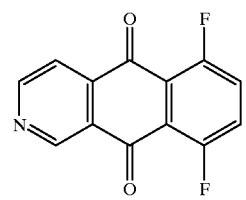

(VIII)

The compound of formula (VIII) is then reacted using the following procedure:

a) reaction of (VIII) with sodium methoxide in methanol and THF, to obtain the intermediate (IX):

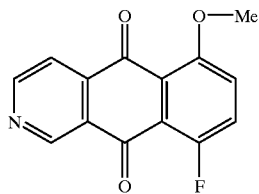

(IX)

b) demethylation of the methoxyl group of the intermediate (IX) with methanesulfonic acid at about 110° C., to obtain, after crystallization from isopropanol, the intermediate (X):

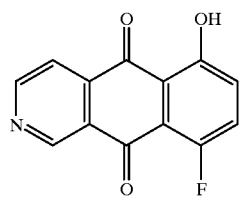

(X)

c) reaction of the compound (X) with p-toluenesulfonyl chloride in pyridine at room temperature, to obtain the desired intermediate (II').

The intermediate of formula (II) in which U is chlorine and W is fluorine can be prepared according to the following reaction sequence:

(a) reaction of 3-chloropyridine with carbon dioxide, at temperatures ranging between −50° C. and −78° C., in an inert solvent such as an ether (THF) and in the presence of a base such as butyl lithium or lithium diisopropilamide, to give 3-chloro-nicotin-4-carboxylic acid;

(b) esterification of 3-chloro-nicotin-4-carboxylic, acid to give methyl-3-chloro-isonicotinate. A reagent which can be used is diazomethane, in an inert solvent such as ethyl ether.

(c) reaction of methyl-3-chloro-isonicotinate with an organo zinc (obtained from 2-fluoro-5-chloro α-bromotolune and reactive zinc, in THF and at about 0° C.) [Knochel, P. et al., Chem. Rev. 93, 2117–2188 (1993); Negishi et al., J. Org. Chem., 42, 1821–1823 (1977)], in the presence of dichlorobis(triphenylphosphine)nikel as the catalyst, to give the intermediate of formula (XI):

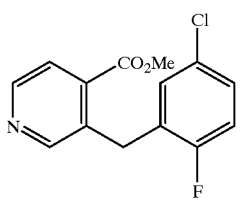

(XI)

Said reaction can be carried out in an inert solvent such as an ether (THF) and at temperature between −10° C. and room temperature;

(d) hydrolysis of the intermediate (XI) methyl ester to give the corresponding acid derivative. The conditions used in the hydrolysis reaction are the use of an alkali metal hydroxide (for example, sodium hydroxide) in aqueous and/or alcohol medium and at temperatures ranging between room temperature and the boiling temperature of the solvent or of the mixture of solvents;

(e) cyclization of the acid obtained in step (d) to give the intermediate (II) with U=chlorine and W=fluorine, in the presence of fuming sulfuric acid and/or oleum and at temperatures of 100–130° C.

Alternatively, the intermediate of formula (II) in which U is chlorine and W is F can be obtained using the following scheme:

(a) bromination of 2-chloro-5-fluorotoluene with N-bromo-succinimide in the presence of catalytic amounts of aza-isobutyronitrile or dibenzoyl peroxide, in an inert solvent such as carbon tetrachloride and at temperature ranging between room temperature and 80° C.

(b) reaction of α-bromo-2-chloro-5-fluorotoluene obtained in step (a) in tetrahydrofuran with activated zinc; subsequent reaction of the resulting organo zinc with N-phenoxycarbonyl nicotinium chloride (obtained in turn from methyl nicotinate by acylation with phenylchloroformate in tetrahydrofuran), to obtain the intermediate (XII):

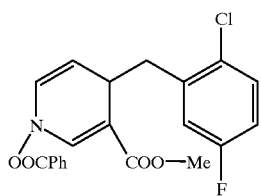

(XII)

Said reaction can be carried out at temperatures ranging between –5° C. and room temperature.

(c) aromatization of the dihydropyridine ring to pyridine in the intermediate (XII), for example with sulfur in decaline under reflux.

(d) hydrolysis of the methyl ester with an alcoholic solution of an alkali or alkaline-earth metal hydroxide. For example, sodium hydroxide in methanol can be used as the reagent.

(e) cyclization of the acid derivative obtained in (d) in oleum (20% $SO_3$) at high temperatures (100–150° C.), to obtain the intermediate (II).

The compound of formula (VI) can be obtained starting from 3,4-pyridine-dicarboxylic acid (commercially available) by reaction with a suitable dehydrating agent, such as a carboxylic acid anhydride (acetic or trifluoroacetic anhydride), a carbodiimide (N,N'-dicyclohexylcarbodiimide) or similar reagents.

A preferred method is the treatment of 3,4-pyridine-dicarboxylic acid with acetic anhydride at about 110° C.

The salts of the compound of formula (I) can be converted one into another according to conventional methods, well known to those skilled in the art.

BIOLOGICAL ACTIVITY OF THE COMPOUND OF THE INVENTION

The evaluation of the biological activity for the compound of this invention was performed "in vitro" and "in vivo" following the protocols developed by the U.S. National Cancer Institute.

The evaluation of the "in vitro" cytotoxic activity was performed using a human colon adenocarcinoma cell line (Lovo) isolated from a metastatic nodule. The compound was tested according to the MTT assay (Mosman, T. "Rapid Colorimetric Assay for Cellular Growth and Survival: Application to Proliferation and Cytotoxicity Assay", J. Immunol. Methods, (1983), 65, 55–63; Green, L. M., "Rapid Colorimetric Assay for Cell Viability; Application to the Quantitation of Cytotoxic and Growth Inhibitory Lymphokines", J. Immunol. Methods, (1984), 70, 257–268) in comparison with mitoxantrone, doxorubicine and CI-941. As reported in table I, the compound of the invention has shown an activity comparable to doxorubicin.

Studies of the biological activity "in vivo" were carried out using the P 388 murine leukemia model. P 388 Murine leukemia cells were intravenously (iv) injected in CD2F1 mice. Treatment was initiated approximately 24 hours after tumor transplantation and dosages of the product were administered iv according to preestablished protocols, usually at 3-day intervals. The studies were done over a 60 day period and the date of death for each animal was recorded. The % T/C was determined using the median survival time (MST) for each group according to the formula $$T/C\% = [(MST_{treated})/(MST_{controls})] \times 100$$

The compound of the invention turned out to be active in increasing the survival time of the treated animals compared with the controls (untreated animals). Moreover, the compound of the invention proved to be better tolerated than mitoxantrone (Table II).

Further in vivo studies of biological activity of the compound of the invention were carried out using two human tumor xenografts, the human breast MX-1 tumor and the ovary tumor A2780 (Table II). The compound of the invention has evidenced an activity equal if not higher than CI-941, expressed as "tumor weight inhibition". The "tumor weight inhibition" can be evaluated as follows:

TWI%=100-[(average relative weight of the tumor$_{treated}$/average relative weight of the tumor$_{controls}$)100]

Moreover, the compound of the invention, contrary to CI-941, has shown a significant number of complete tumor regressions at the tested doses, in the absence of toxic effects. By tumor regression, it is meant the reduction of the tumor mass measured 30 days after the end of the treatment compared with the tumor starting weight. Complete tumor regression means the disappearance of the tumor mass.

Therefore, on the basis of the results shown, the compound of the invention is expected to be active in man against leukemias and solid tumors sensitive to the treatment with antitumor antibiotics and anthracenediones.

The compound of the invention can therefore be used as active ingredient in therapeutical compositions for the regression and/or the treatment of tumors in mammals, when administered in amounts ranging between 0.5 and 20 mg/kg body weight. A preferred dosage regimen can be between 1 and 18 mg/kg body weight of the mammal. More particularly, a preferred dosage regimen for man could range between 5 and 200 mg/m2 body area.

The dosage can be adjusted to be compatible with other treatment regimens, as for example radiotherapy.

Table I—In vitro biological evaluation of the compound of the invention (I), mitoxantrone, doxorubicin and CI-941 in a human colon adenocarcinoma cell line (LoVo) 1 hour after treatment with the medicament

| Compound | IC$_{50}$ ± S.D. (µg/ml) |
|---|---|
| compound (I) | 0.54 ± 0.17 |
| mitoxantrone | 0.026 ± 0.017 |
| doxorubicin | 0.7 ± 0.49 |
| CI-941 | 0.039 ± 0.035 |

TABLE II

In vivo biological evaluation of the compound of the invention (I), mitoxantrone and of CI-941 against murine leukemia P388 and human tumor xenografts (MX-1 and A 2780) models in mice

| | P388 iv/iv + 1,4,7 | | | MX-1 sc/iv q7dx3 | | | A 2780 sc/iv q4dx3 | | | |
|---|---|---|---|---|---|---|---|---|---|---|
| Compound | dose (mg/kg) | T/C % | Tox. | dose (mg/kg) | TWI % | Tox. | dose (mg/kg) | TWI % | Tox. | Tumor regression |
| compound (I) | 7.5 | 167 | 0/8 | 8.9 | 78 | 0/5 | 7.5 | 99 | 0/7 | 4/7 |
| | | | | 17.5 | 96 | 0/5 | 9.7 | 100 | 0/7 | 6/7 |
| mitoxantrone | 3 | 195 | 16/284 | 4.5 | 74 | 16/60 | — | — | — | — |
| CI-941 | 6 | 133 | 0/8 | 9 | 83 | 0/7 | 8 | 87 | 0/7 | 0/7 |
| | 9 | 144 | 0/8 | 13.5 | 93 | 0/40 | 10.4 | 97 | 0/7 | 0/7 |
| | 13.5 | 133 | 0/8 | 17.5 | 97 | 9/33 | 13.5 | 100 | 5/7 | 1/7 |

The pharmaceutical compositions containing the compound of formula (I) are comprised within the invention. These pharmaceutical compositions can contain any amount of compound of formula (I) capable of exerting an antitumor activity in mammals against tumor sensitive to the treatment with doxorubicin, anthracenediones and anthrapyrazoles.

The pharmaceutical compositions can contain, in addition to the compound of formula (I), pharmaceutically compatible excipients, suitable for any administration route, such as the oral, parenteral, intravenous, endodermic, subcutaneous or topical administrations, in liquid or solid form.

An administration route of the compound of formula (I) is the oral one. Oral compositions will generally include an inert diluent or a carrier edible. They can be included in gelatin capsules or compressed into tablets. Other oral administration forms are capsules, pills, elixirs, suspensions or syrups.

The tablets, pills, capsules and similar compositions can contain the following ingredients (in addition to the active ingredient): a binder, such as microcrystalline cellulose, tragacanth or gelatin; an excipient such as starch or lactose; a disintegrating agent such as alginic acid, primogel, maize starch and the like; a lubricant such as magnesium stearate; a fluidifier such as colloidal silicon dioxide; a sweetening agent such as sucrose or saccharine or a flavouring agent such as mint flavour, methyl salicylate or orange flavour. When the composition selected is in form of capsules, it can contain in addition a liquid carrier such as a fat oil. Other compositions can contain various materials which change the physical form thereof, for example coating agents (for tablets and pills) such as sugar or shellac. The materials used in the preparation of the compositions should be pharmaceutically pure and non toxic at the used dosages.

For the preparation of pharmaceutical compositions for the parenteral administration, the active ingredient can be included in solutions or suspensions, which can comprise in addition the following components: a sterile diluent such as water for injections, saline solution, oils, polyethylene glycols, glycerin, propylene glycol or other synthetic solvents; antibacterial agents such as benzyl alcohol; antioxidants such as ascorbic acid or sodium bisulfite; chelating agents such as ethylenediaminotetraacetic acid; buffers such as acetates, citrates or phosphates and agents for adjusting the tonicity of the solution, such as sodium chloride or dextrose. The parenteral preparation can be included in ampoules, mono-dose syringes, glass or plastic vials.

SYNTHESIS OF THE COMPOUND OF THE INVENTION

Preparation 1

3,4-Pyridine-dicarboxylic acid anhydride (VI)

A mixture of 3,4-pyridine-dicarboxylic acid (15 g) and acetic anhydride (30 ml) is refluxed for 2 hours. The acetic anhydride in excess is distilled off and the residue is purified by sublimation (123° C. at 3 mmHg) to give 10.1 g of 3,4-pyridine-dicarboxylic acid anhydride, a white solid, m.p. 74–76° C.

$^1$H-NMR (200 MHz) in CDCl$_3$: 7.94 ppm (d, 1H); 9.24 ppm (d, 1H); 9.39 ppm (s, 1H).

Preparation 2

Mixture of (VIIa) and (VIIb)

A mixture of 3,4-pyridine-dicarboxylic acid anhydride (5 g) and aluminium trichloride (17.5 g) in 1,4-difluorobenzene (65 ml) is heated on an oil bath at 110° C. for 22 hours. 1,4-difluorobenzene in excess is recovered by distillation. The residue is cooled in an ice bath and added with water/ice (75 ml) and concentrated hydrochloric acid (6.3 ml). The precipitated solid is filtered and dried to give an about 4:1 mixture of 4-(2,5-difluorobenzoyl)nicotinic acid and 3-(2,5-difluorobenzoyl)isonicotinic acid (7.7 g) as a white powder, which can be recrystallized from acetonitrile and water; m.p. 214–217° C.

$^1$H-NMR (200 MHz) in d6-DMSO: 7.4 ppm (m); 7.5 ppm (m); 7.9 ppm (m); 8.8 ppm (d); 8.9 ppm (d); 9.15 ppm (s).

Preparation 3

6,9-difluorobenzo[g]isoquinolin-5,10-dione (II')

A solution of the mixture of (VIIa) and (VIIb) from preparation 2 (61.07 g) in oleum (20% SO$_3$, 100 ml) is heated at 140° C. and further oleum is added in four portions (13.2 ml each) at 20 minute intervals. After the last addition, the mixture is heated for a further 20 minutes, then is cooled at room temperature and added with a mixture of ice (1500 ml), water (1500 ml) and 35% sodium hydroxide (350 ml). The mixture is extracted with methylene chloride (1×1000 ml followed by 3×500 ml). The combined organic extracts are washed with water (2×1000 ml), dried over sodium sulfate and the solvent is removed under reduced pressure. The resulting dark red solid (56 g) is dissolved in hot THF (840 ml) and decolourized with active charcoal (8.4 g). After 30 minutes the still warm mixture is filtered and the filtrate is concentrated to a volume of 200 ml. The resulting precipitate is separated by filtration to give 43 g of product, m.p. 201–203 ° C.

By concentration of the mother liquors to a volume of 70 ml, a second crop of product is obtained (3.35 g), m.p. 200–202° C.

Preparation 4

9-fluoro-6-methoxybenzo[g]isoquinolin-5,10-dione

A solution of sodium methoxide, freshly prepared under nitrogen atmosphere from anhydrous methanol (97.6 ml) and sodium (2.024 g), is dropped in a time of 2 hours and 35 minutes into a solution of 6,9-difluorobenzo[g]isoquinolin-5,10-dione (19.615 g, preparation 3) in anhydrous THF (883 ml), under stirring and at room temperature. At the end of the addition, the reaction mixture is concentrated to half the starting volume, then is kept at 18° C. for 30 minutes. The separated solid is filtered and washed with 100 ml of THF, then it is suspended in water (80 ml), left overnight under stirring and filtered again to give 9.3 g of crude product, which is suspended in methylene chloride (45 ml) and refluxed for 30 minutes. After cooling at room temperature, the product is filtered and the separated solid is washed with methylene chloride (5×3 ml), then dried under vacuum at 40° C., to obtain 8.65 g of pure product, m.p. 248–250° C.

$^1$H-NMR (200 MHz) in $CDCl_3$: 4.05 ppm (s, 3H); 7.40 ppm (dd, J=9.39, 3.91 Hz, 1 H); 7.55 ppm (dd, J=10.37, 9.39 Hz, 1H); 8.00 ppm (dd, J=5.09, 0.78 Hz, 1H); 9.05 ppm (d, J=5.09 Hz, 1H); 9.48 ppm (d, J=0.78 Hz, 1H).

Preparation 5

9-fluoro-6-hydroxybenzo[g]isoquinolin-5,10-dione

A mixture of 29 g of 9-fluoro-6-methoxybenzo[g]isoquinolin-5,10-dione in 145 ml of methanesulfonic acid is heated at 110° C., with stirring and under inert gas atmosphere, for about 2 hours, then added to 3000 ml of water. After 1 hour under stirring, the formed precipitate is filtered, washed with about 300 ml of water, taken up into a further 2000 ml of water and, after stirring for 30 minutes, filtered again. The mother liquors are extracted with 500 ml of ethyl acetate. The organic phase is separated and the solvent is evaporated under reduced pressure. The residue (3 g) is combined with the first crystallization crop and the whole is taken up into 500 ml of isopropanol. After an hour under stirring, the crystallized product is filtered, to obtain 24.16 g of product, m.p. 189–192° C.

Preparation 6

9-fluoro-6-(p-toluenesulfonyloxy)benzo-[g]isoquinolin-5,10-dione

A solution of 9-fluoro-6-hydroxybenzo[g]isoquinolin-5,10-dione (18 g) and triethylamine (17.51 ml) in methylene chloride (540 ml) is added with 21.37 g of tosyl chloride, at room temperature, with stirring and under inert gas atmosphere. After about 8 hours the reaction mixture is washed with 200 ml of water and the washings are extracted with methylene chloride. The combined organic phases are dried over sodium sulfate and the solvent is evaporated under reduced pressure, to obtain 80 g of residue. Said residue is taken up into 294 ml of hexane and left under stirring at room temperature for 1 hour, then is filtered and washed on the filter with 200 ml of hexane. The resulting solid (29 g) is crystallized at 40° C. from a mixture of methylene chloride (160 ml) and isopropanol (60 ml). The warm solution is filtered over a glass fiber filter and concentrated to a residual volume of about 120 ml. The product crystallizes which, after 2 hours under stirring, is filtered to obtain a first crop of g 12.92. By further concentration of the crystallization mother liquors to half the volume a second crop of product is obtained (7.65 g). m.p. 170–172° C.

Preparation 7

2-[2-[(2-hydroxyethyl)amino]ethyl]-5-(p-toluenesulfonyloxy)indazolo[4,3-gh]isoquinolin-6(2H)-one A solution of N-[2-[(2-hydroxyethylamino)ethyl]] hydrazine (J. Het. Chem., 26, 85 (1989); 0.179 g) in absolute ethanol (0.5 ml) is dropped into a solution of 9-fluoro-6-(p-toluenesulfonyloxy)benzo[g]isoquinolin-5,10-dione (0.2 g; preparation 6) and triethylamine (0.073 g) in 2 ml of THF, kept under stirring and at room temperature. After 2 hours, a second portion of N-[2-[(2-hydroxyethylamino)ethyl]] hydrazine (0.179 g) in 0.5 ml of absolute ethanol is added and after a further 2 hours the reaction mixture is concentrated to a volume of about 1 ml. 20 ml of water are added and the resulting mixture is kept under stirring at room temperature overnight, then the separated solid is filtered, dried under vacuum at 40° C. and finally taken up into hot ethyl acetate to obtain 0.06 g of product, m.p. 131–133° C.

$^1$H-NMR (200 MHz) in $d6$-DMSO/$D_2O$: 2.45 ppm (s, 3H); 2.62 ppm (t, 2H); 3.13 ppm (t, 2H); 3.40 ppm (t, 2H); 4.65 ppm (t, 2H); 7.25 ppm (d, 1H); 7.40 ppm (d, 2H); 7.75 ppm (d, 2H); 7.95 ppm (d, 1H); 8.15 ppm (d, 1H); 8.80 ppm (d, 1H); 9.40 ppm (s, 1H).

Preparation 8

2-[2-[N-[(1,1-dimethylethoxy)carbonyl]-N-(2-hydroxyethyl)amino]ethyl]-5-(p-toluenesulfonyloxy)-isoquino[8,7,6,-cd]indazolo-6(2H)-one A solution of ditert-butyl dicarbonate (1.12 g) in THF (20 ml) and water (4 ml), kept under stirring, is added in a time of 2 minutes, with 2.132 g of solid 2-[2-[(2-hydroxyethyl)amino]ethyl]-5-(p-toluenesulfonyloxy)indazolo[4,3-gh]isoquinolin-6(2H)-one (preparation 7), in portions. The reaction mixture is kept at room temperature under stirring for 1 hour, then is concentrated to small volume. The residue is repeatedly taken up into ethanol and concentrated nearly to dryness, thereby removing the residual water. The resulting solid is ground with hot methyl tertbutyl ether, then methylene chloride is added to complete dissolution of the solid. Methylene chloride is then distilled off under a slight nitrogen stream. The mixture is left to cool at room temperature and the solid is separated by filtration, washed with abundant methyl tertbutyl ether and dried under vacuum at 40° C. 1.91 g of product as a green solid are obtained, m.p. 175–178° C.

$^1$H-NMR (200 MHz, 323° K) in $d6$-DMSO: 9.43 ppm (s, 1H); 8.85 ppm (d, 1H); 8.17 ppm (d, 1H); 7.98 ppm (d, 1H);

7.78 ppm (d, 2H); 7.50–7.30 ppm (m, 3H); 4.80 ppm (t, 2H); 4.67 ppm (br. s, 1H); 3.75 ppm (br. s, 2H); 3.57–3.35 ppm (br. m, 2H); 3.30–2.95 ppm (br. m, 2H); 2.38 ppm (s, 3H); 1.17 ppm (br. s, 4H); 0.90 ppm (br. s, 5H).

Preparation 9

2-[2-[N-[(1,1-dimethylethoxy)carbonyl]-N-(2-hydroxyethyl)amino]ethyl]-5-[(N-methyl-N-[(1,1-dimethylethoxy)carbonyl]amino)ethylamino]isoquino[8,7,6,-cd]indazolo-6(2H)-one A mixture of 2-[2-[N-[(1,1-dimethylethoxy)carbonyl]-N-2-hydroxyethyl)amino]ethyl]-5-(p-toluenesulfonyloxy)isoquino[8,7,6,-cd]indazolo-6(2H)-one (0.74 g) and N-methyl-N-BOC ethylenediamine (1.561 g; Saari, W. S. et al., J. Med. Chem., 33, 97–101 (1989)) in 6 ml of pyridine is heated at 65° C. for 6 hours and 30 minutes. The whole solid dissolves. The solution is heated at 100° C. for 2 hours and 30 minutes, then the reaction mixture is concentrated to small volume. The residue is taken up with 100 ml of methylene chloride and 50 ml of 1N aqueous sodium hydroxide, then the basic aqueous phase is separated and extracted with methylene chloride (2×50 ml). The organic extracts are washed with a mixture of water (50 ml) and a $NaH_2PO_4$ saturated solution (25 ml), dried over sodium sulfate and the solvent is removed under reduced pressure. The residue (950 mg) is purified by silica gel chromatography (70 g; eluent methylene chloride/methanol 97:3–95:5), to obtain 585 mg of product as an orange foam.

$H^1$-NMR (200 MHz, 333° K) in d6-DMSO: 1.17 ppm (s br., 9H); 1.33 ppm (s, 9H); 2.87 ppm (s, 3H); 3.05–3.20 ppm (m, 2H); 3.45 ppm (q, 2H); 3.52 ppm (t, 2H); 3.72 ppm (q, 2H); 3.76 ppm (t, 2H); 4.46 ppm (t br., 1H); 4.76 ppm (t, 2H); 7.27 ppm (d, 1H); 7.98 ppm (d, 1H); 8.20 ppm (dd, 1H); 8.79 ppm (d, 1H); 9.20 ppm (t br., 1H); 9.51 ppm (d, 1H).

Preparation 10

2-[2-[N-(2-hydroxyethyl)amino]ethyl]-5-[(N-methyl-N-[( 1,1-dimethylethoxy)carbonyl]amino)ethyl-amino]isoquino[8,7,6,-cd]indazolo-6(2H)-one A solution of N-methyl-N-BOC ethylenediamine (2.12 g) in 7 ml of anhydrous pyridine is added with 710 mg of 2-[2-[(2-hydroxyethyl)amino]ethyl]-5-(p-toluenesulfonyloxy)indazolo[4,3-gh]isoquinolin-6(2H)-one (preparation 7), then the reaction mixture is heated at 50° C., with stirring and under nitrogen atmosphere for 22 hours. After that, the mixture is heated at 70° C. for one more hour, then the solvent is evaporated under reduced pressure at 40° C. The residue is partitioned between 25 ml of 0.1 N sodium hydroxide and 75 ml of methylene chloride, then the aqueous phase is extracted with methylene chloride (2×25 ml). The combined organic phases are washed twice with brine (25 ml), dried over sodium sulfate and the solvent is evaporated under reduced pressure, to obtain about 2 g of a brown oil. The residue is purified by silica gel chromatography (50 g; eluent methylene chloride/methanol/ammonium hydroxide 95:5:0–85:15:0.6) and by subsequent crystallization from methylene chloride/methyl tertbutyl ether, to obtain 339 mg of product.

m.p. 139.5–141.5° C.

$H^1$-NMR (200 MHz) in $CDCl_3$: 1.48 ppm (s, 9H); 2.85 ppm (t, 2H); 2.94 ppm (s, 3H); 3.30 ppm (t, 2H); 3.50–3.75 ppm (m, 6H); 4.66 ppm (t, 2H); 6.95–7.20 ppm (m, 1H); 7.70 ppm (d, 1H); 8.27 ppm (d, 1H); 8.80 ppm (d, 1H); 9.28 ppm (t br., 1H); 9.51 ppm (d, 1H).

EXAMPLE 1

2-[2-[N-(2-hydroxyethyl)amino]ethyl]-5-[(N-methylamino)ethylamino]isoauino[8,7,6,-cd]indazolo-6(2H)-one trihydrochloride A solution of 2-[2-[N-[(1,1-dimethylethoxy)carbonyl]-N-(2-hydroxyethyl)amino]ethyl]-5-[(N-methyl-N-[(1,1-dimethylethoxy)carbonyl]amino)ethylamino]isoquino[8,7,6,-cd]indazolo-6(2H)-one (563 mg; preparation 9) in 20 ml of absolute ethanol is added with 5 ml of a 4.11 M solution of hydrogen chloride in absolute ethanol. The resulting dark red solution is kept under stirring, at room temperature and under nitrogen atmosphere, for about 20 hours. The formed red solid is filtered, washed thoroughly with ethanol and dried under vacuum a 50° C., to obtain 414 mg of product.

m.p. 220–222° C. (decomposition)

$H^1$-NMR (200 MHz) in $D_2O$: 2.80 ppm (s, 3H); 3.35 ppm (q, 2H); 3.45 ppm (t, 2H); 3.83 ppm (t, 2H); 3.87–3.93 ppm (m, 2H); 4.00 ppm (t, 2H); 4.97 ppm (t, 2H); 7.11 ppm (d, 1H); 7.91 ppm (d, 1H); 8.39 ppm (d, 1H); 8.77 ppm (d, 1H); 9.34 ppm (s, 1H).

EXAMPLE 2

2-[2-[N-(2-hydroxyethyl)amino]ethyl]-5-[(N-methylamino)ethylamino]isoquino[8,7,6,-cd]indazolo-6(2H)-one trihydrochloride A suspension of 2-[2-[N-(2-hydroxyethyl)amino]-ethyl]-5-[(N-methyl-N-[(1,1-dimethylethoxy)carbonyl]amino)ethylamino]isoquino[8,7,6,-cd]indazolo-6(2H)-one (320 mg; preparation 10) in 14 ml of absolute ethanol is added, during a minute, with 5 ml of a 6.5 M solution of hydrogen chloride in absolute ethanol, keeping the temperature at about 0° C. A red solid precipitates, which is partially redissolved by addition of 1.5 ml of water. The reaction mixture is kept at room temperature for about 23 hours, then heated at about 55° C. for 2 hours. After that, the red precipitate is filtered off under nitrogen atmosphere, thereafter washed with ethanol and dried under vacuum for 1 hour at 40° C., then at room temperature. 271 mg of product as a red solid are obtained, m.p. 220–222° C. (decomposition)

$H^1$-NMR (200 MHz) in $D_2O$: 2.80 ppm (s, 3H); 3.35 ppm (q, 2H); 3.45 ppm (t, 2H); 3.83 ppm (t, 2H); 3.87–3.93 ppm (m, 2H); 4.00 ppm (t, 2H); 4.97 ppm (t, 2H); 7.11 ppm (d, 1H); 7.91 ppm (d, 1H); 8.39 ppm (d, 1H); 8.77 ppm (d, 1H); 9.34 ppm (s, 1H).

It is claimed:

1. The compound of formula (I):

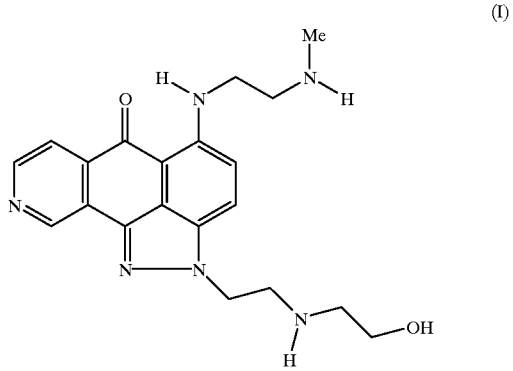

as a free base and the pharmaceutically acceptable acid addition salts thereof.

2. The compound of formula (I) as the trihydrochloride.

3. A process for the preparation of the compound of formula (I) or of the salts thereof, which process comprises the following steps:

(a) reaction of an intermediate of formula (II):

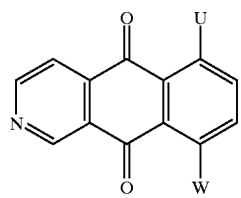

(II)

wherein U is selected from the group consisting of fluorine, chlorine, para-toluenesulfonyloxy, methanesulfonyloxy and W is fluorine or chlorine, with the proviso that U and W cannot be at the same time chlorine, with an hydrazine of formula (III):

H$_2$N—NH—CH$_2$—CH$_2$—N(—P)—CH$_2$CH$_2$—OP'    (III)

wherein P and P' can be independently hydrogen or a (C$_1$–C$_3$)-acyl, (C$_1$–C$_4$)-alkoxycarbonyl or aralkyloxycarbonyl group stable in the reaction conditions;

(b) reaction of the compound obtained in step (a) with an amine of formula (V):

H$_2$N—CH$_2$CH$_2$—N(—P)Me    (V)

in which P is as above defined;

(c) cleavage of any (C$_1$–C$_3$)-acyl, (C$_1$–C$_4$)-alkoxycarbonyl or aralkyloxy-carbonyl present.

4. The process of claim 3, in which U is para-toluenesulfonyloxy and W is fluorine.

5. The process of claim 3, wherein said P and P' are independently hydrogen or an acetyl, tert-butoxycarbonyl or benzyloxycarbonyl group.

6. A pharmaceutical composition comprising an effective amount of a compound of claim 1 in admixture with a pharmaceutically acceptable carrier or excipient.

7. A method of treating leukemia, colon tumor, breast tumor, or ovary tumor in a mammal requiring said treatment, comprising administering to said mammal an effective amount of a compound of claim 1.

* * * * *

UNITED STATES PATENT AND TRADEMARK OFFICE
CERTIFICATE OF CORRECTION

PATENT NO. : 6,034,092
DATED : March 7, 2000
INVENTOR(S) : Ernesto Menta et al.

It is certified that error appears in the above-identified patent and that said Letters Patent is hereby corrected as shown below:

Item [73] after "Novuspharma S.p.A., Milan, Italy" insert --The University of Vermont and State Agricultural College, Burlington, Vermont--.

Signed and Sealed this

Third Day of July, 2001

*Attest:*

*Attesting Officer*

NICHOLAS P. GODICI
*Acting Director of the United States Patent and Trademark Office*